United States Patent
Brandl et al.

(10) Patent No.: US 11,883,229 B2
(45) Date of Patent: Jan. 30, 2024

(54) METHODS AND SYSTEMS FOR DETECTING ABNORMAL FLOW IN DOPPLER ULTRASOUND IMAGING

(71) Applicant: GE Precision Healthcare LLC, Milwaukee, WI (US)

(72) Inventors: Helmut Brandl, Pfaffing (AT); Heinz Schmied, Tiefgraben (AT); Christian Wallinger, Frankenmarkt (AT); Christian Fritz Perrey, Mondsee (AT); Yelena Viktorovna Tsymbalenko, Mequon, WI (US)

(73) Assignee: GE PRECISION HEALTHCARE LLC, Milwaukee, WI (US)

(*) Notice: Subject to any disclaimer, the term of this patent is extended or adjusted under 35 U.S.C. 154(b) by 89 days.

(21) Appl. No.: 16/845,813

(22) Filed: Apr. 10, 2020

(65) Prior Publication Data
US 2021/0315538 A1   Oct. 14, 2021

(51) Int. Cl.
| | |
|---|---|
| A61B 8/06 | (2006.01) |
| G16H 30/20 | (2018.01) |
| G16H 50/20 | (2018.01) |
| G16H 50/50 | (2018.01) |
| G16H 40/60 | (2018.01) |
| G16H 15/00 | (2018.01) |
| G01F 1/667 | (2022.01) |
| A61B 8/00 | (2006.01) |

(Continued)

(52) U.S. Cl.
CPC .............. *A61B 8/06* (2013.01); *A61B 5/7267* (2013.01); *A61B 8/0891* (2013.01); *A61B 8/463* (2013.01); *A61B 8/469* (2013.01); *A61B 8/488* (2013.01); *A61B 8/5223* (2013.01); *G01F 1/667* (2013.01); *G16H 15/00* (2018.01); *G16H 30/20* (2018.01); *G16H 40/60* (2018.01); *G16H 50/20* (2018.01); *G16H 50/50* (2018.01); *A61B 8/0866* (2013.01); *A61B 8/5246* (2013.01)

(58) Field of Classification Search
CPC ....... A61B 8/06; A61B 5/7267; A61B 8/0891; A61B 8/463; A61B 8/469; A61B 8/488; A61B 8/5223; A61B 8/0866; A61B 8/565; A61B 8/5246; G01F 1/667; G16H 15/00; G16H 30/20; G16H 40/60; G16H 50/20; G16H 50/50; G16H 30/40; G16H 70/20

See application file for complete search history.

(56) References Cited

U.S. PATENT DOCUMENTS

| | | | | |
|---|---|---|---|---|
| 2006/0052704 A1* | 3/2006 | Baba | ...................... | A61B 8/488 600/453 |
| 2012/0232853 A1* | 9/2012 | Voigt | ...................... | G06T 7/344 703/1 |

(Continued)

*Primary Examiner* — Bo Joseph Peng
(74) *Attorney, Agent, or Firm* — McCoy Russell LLP

(57) ABSTRACT

Various methods and systems are provided for ultrasound imaging. In one embodiment, a method comprises acquiring, via an ultrasound probe, Doppler measurements over a plurality of cardiac cycles, evaluating a flow profile comprising the Doppler measurements to detect an abnormality in the flow profile, and displaying, via a display device, the flow profile with a reference flow profile overlaid thereon. In this way, the attention of a physician evaluating results from an ultrasound imaging examination may be directed to abnormal flow that is potentially indicative of pathologies, thereby enabling earlier and more accurate diagnosis of pathologies.

6 Claims, 8 Drawing Sheets

(51) Int. Cl.
*A61B 8/08* (2006.01)
*A61B 5/00* (2006.01)

(56) References Cited

U.S. PATENT DOCUMENTS

2015/0112901 A1* 4/2015 Singer .................... G16Z 99/00
706/12
2021/0330284 A1* 10/2021 van der Veen ......... A61B 8/463

* cited by examiner

METHODS AND SYSTEMS FOR DETECTING ABNORMAL FLOW IN DOPPLER ULTRASOUND IMAGING

FIELD

Embodiments of the subject matter disclosed herein relate to ultrasound imaging, and more particularly, to methods and systems for detecting abnormal flow via Doppler ultrasound imaging.

BACKGROUND

Medical diagnostic ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Such transducer elements of the ultrasound probe typically include electromechanical elements capable of converting electrical energy into mechanical energy for transmission of ultrasonic waves into patient tissue and mechanical energy back into electrical energy when the reflected ultrasonic waves reach the transducers.

Further, during an ultrasound of a structure through which blood flows (e.g., a heart, vessel, artery, and so on), Doppler ultrasound may be used to obtain an image of blood flow through the vessel or structure (color Doppler) and/or a blood flow velocity waveform (continuous or pulse wave Doppler) for multiple heart cycles. The Doppler spectrum from the continuous or pulse wave Doppler may be displayed via a display device of an ultrasound imaging system alongside ultrasound images such as B-mode images and color Doppler images.

BRIEF DESCRIPTION

In one embodiment, a method comprises acquiring, via an ultrasound probe, Doppler measurements over a plurality of cardiac cycles, evaluating flow profile comprising the Doppler measurements to detect an abnormality in the flow profile, and displaying, via a display device, the flow profile with a reference flow profile overlaid thereon. In this way, the attention of a physician evaluating results from an ultrasound imaging examination may be directed to abnormal flow that is potentially indicative of pathologies, thereby enabling earlier and more accurate diagnosis of pathologies.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
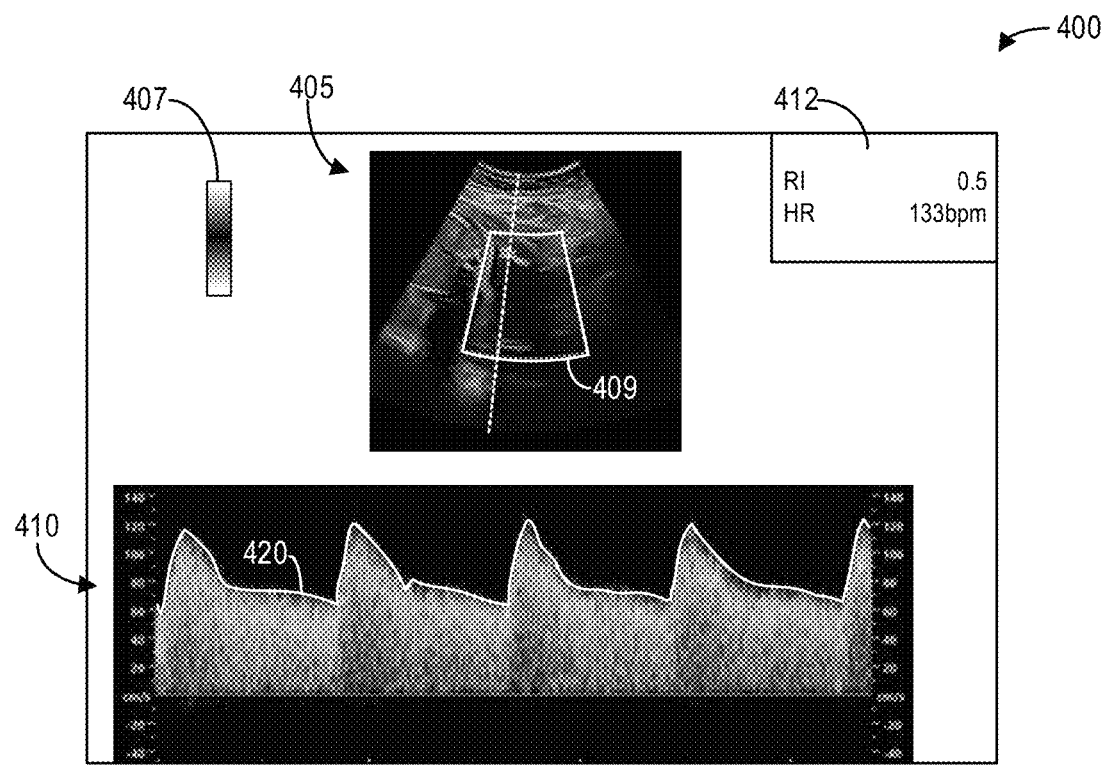
FIG. 4 shows an example display output of a graphical user interface showing a Doppler flow profile for a vessel with a normal flow according to an embodiment.
Figure 5:
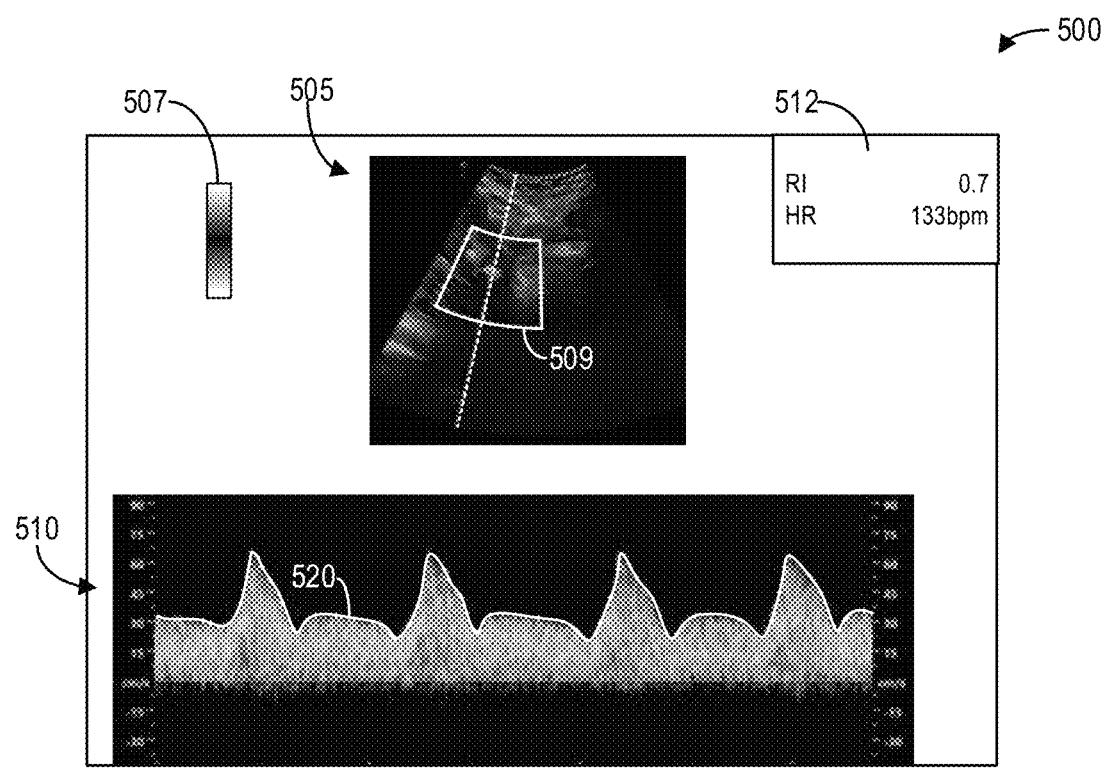
FIG. 5 shows an example display output of a graphical user interface showing a Doppler flow profile for a vessel with a pathological flow according to an embodiment.
Figure 6:
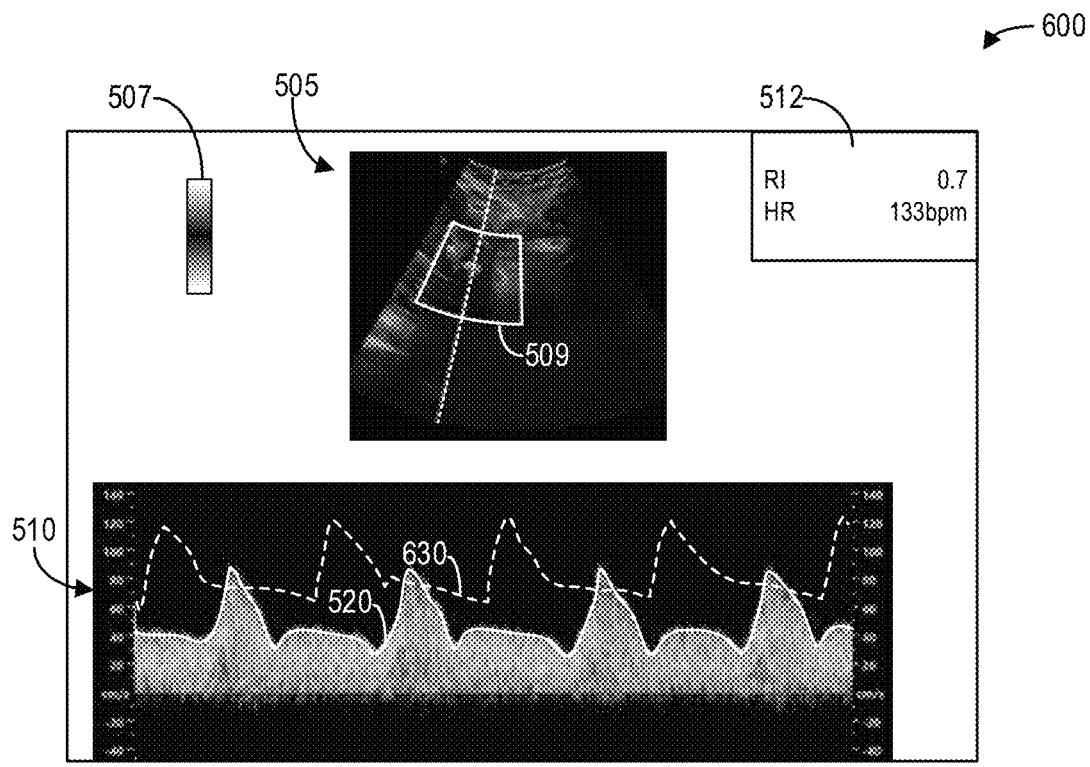
FIG. 6 shows an example display output of a graphical user interface showing the pathological Doppler flow profile of FIG. 5 with a normal flow profile overlaid thereon according to an embodiment.
Figure 7:
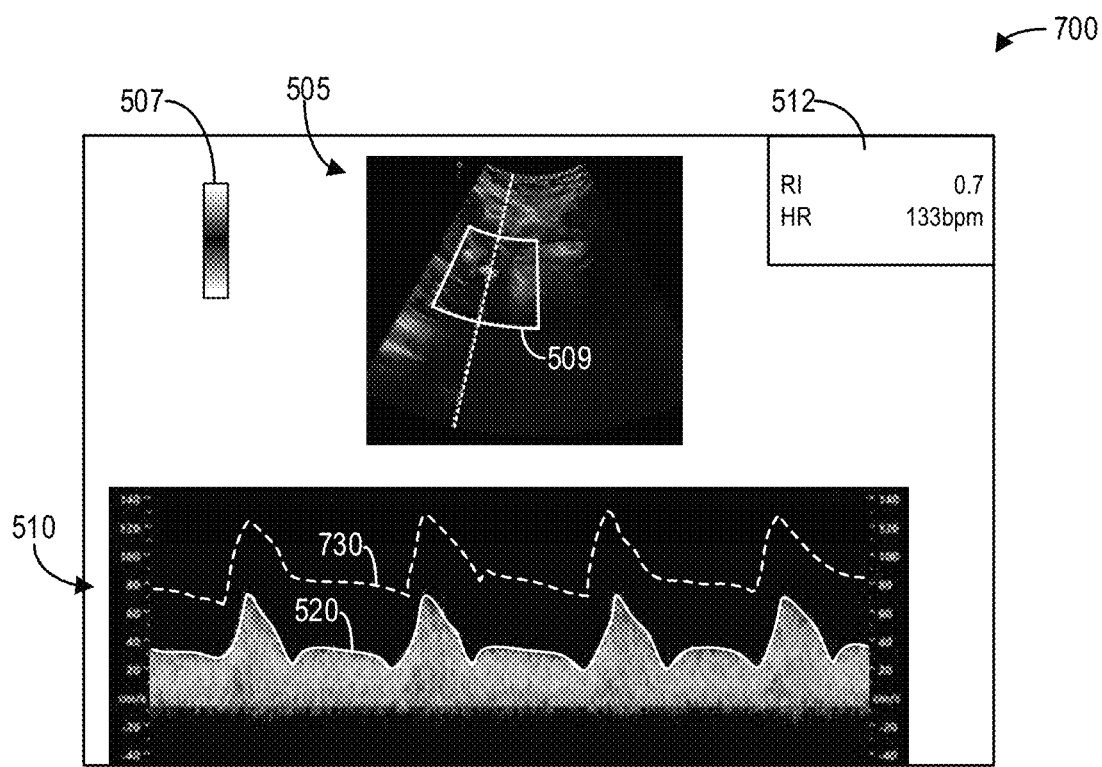
FIG. 7 shows an example display output of a graphical user interface showing the pathological Doppler flow profile of FIG. 5 with a normal flow profile adjusted to match the pathological flow profile and overlaid thereon according to an embodiment.
Figure 8:
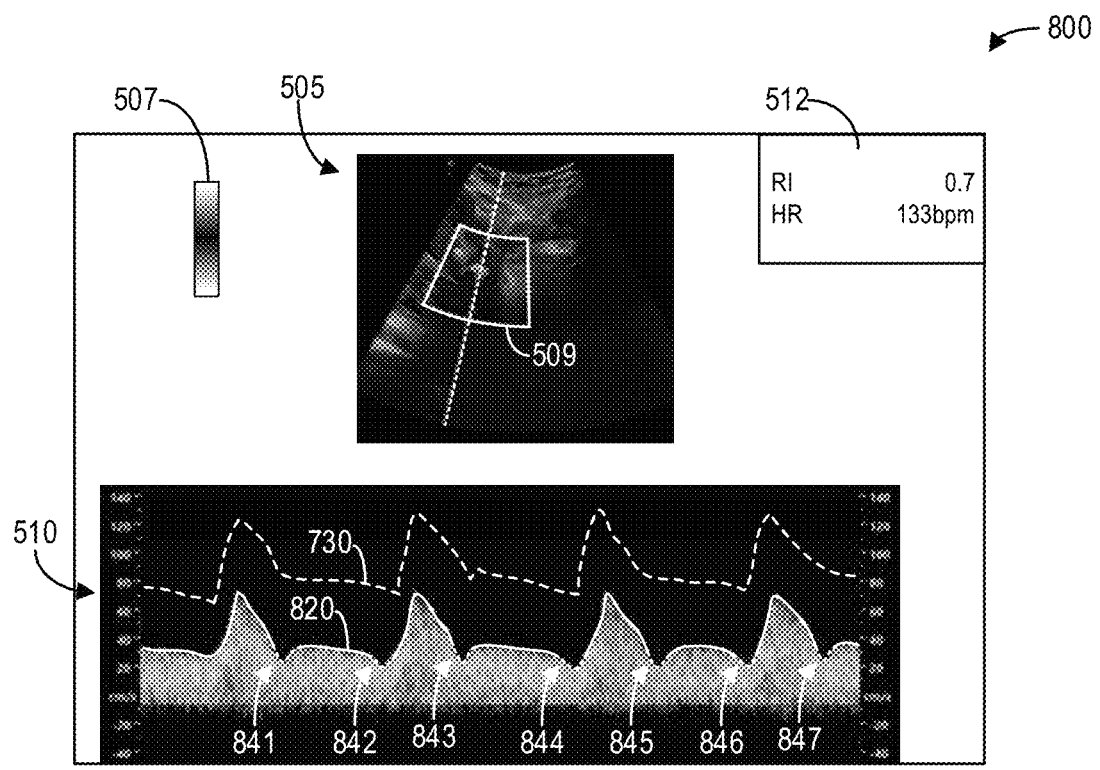
FIG. 8 shows an example display output of a graphical user interface showing the pathological Doppler flow profile of FIG. 5 with display adjustments to highlight differences from a normal flow profile aligned to match the pathological flow profile and overlaid thereon according to an embodiment.
Figure 9:
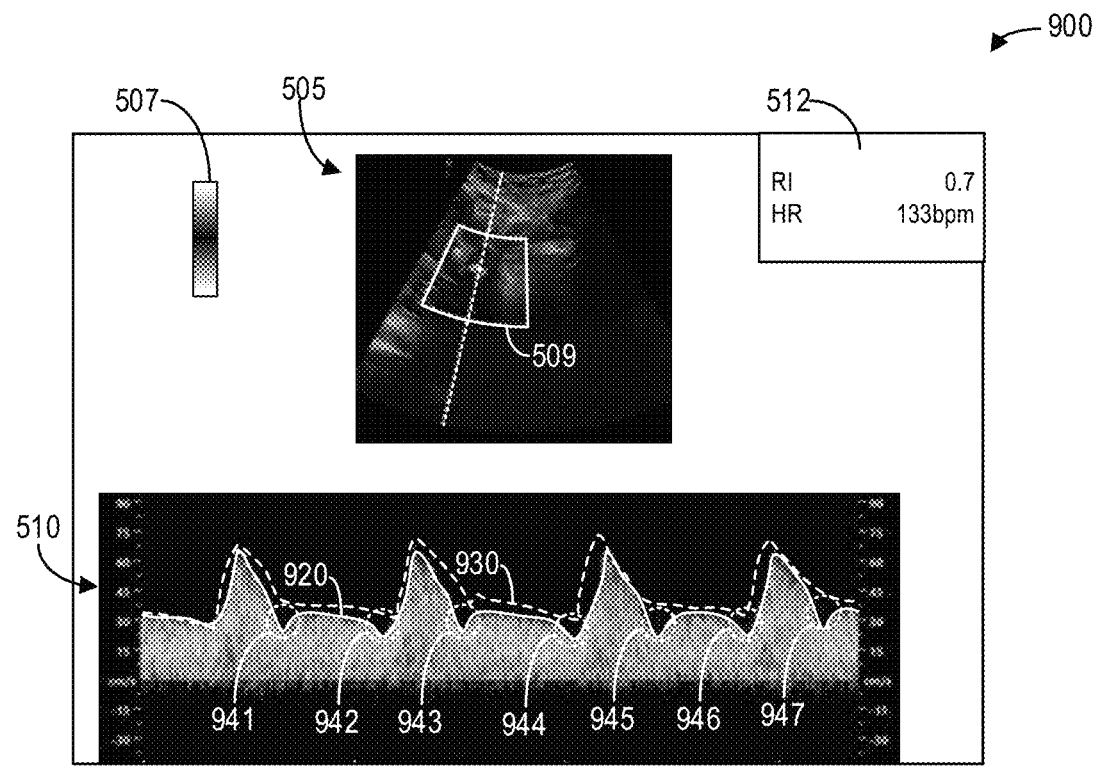
FIG. 9 shows an example display output of a graphical user interface showing the pathological Doppler flow profile of FIG. 5 with a normal flow profile aligned and scaled to match the pathological flow profile and overlaid thereon and with visual indicators of differences with the normal flow profile overlaid thereon according to an embodiment.
Figure 10:
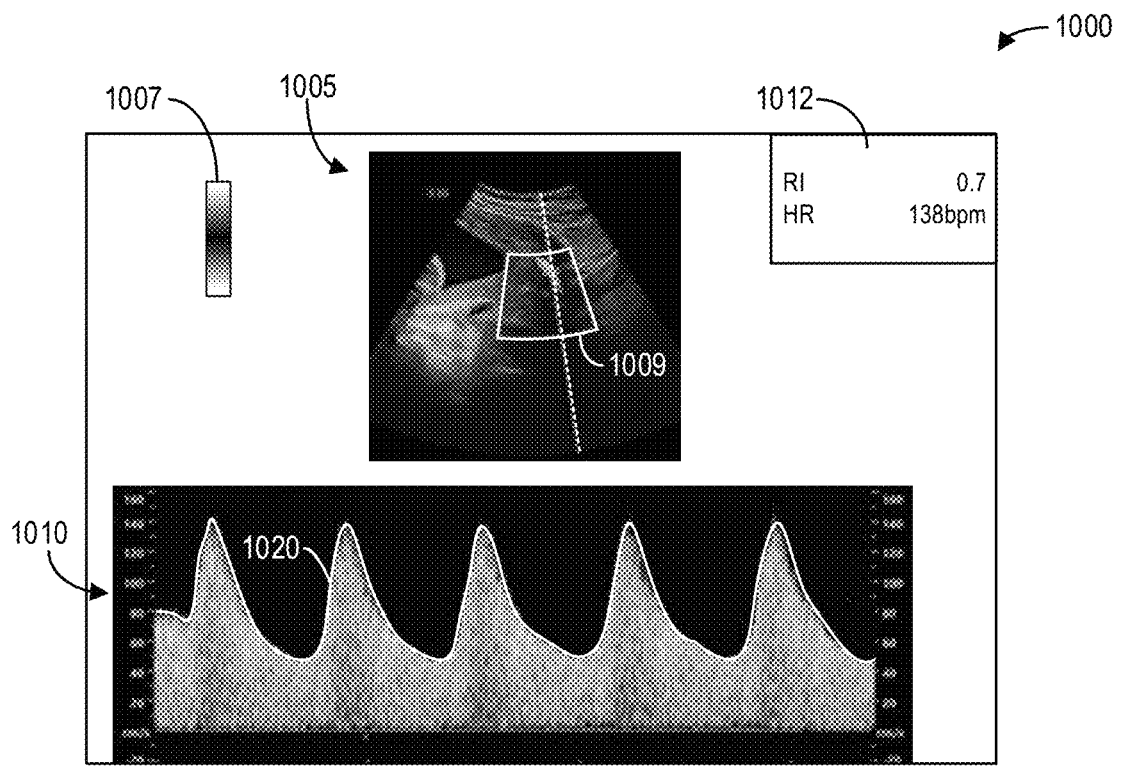
FIG. 10 shows an example display output of a graphical user interface showing another Doppler flow profile for a vessel with a pathological flow according to an embodiment.
Figure 11:
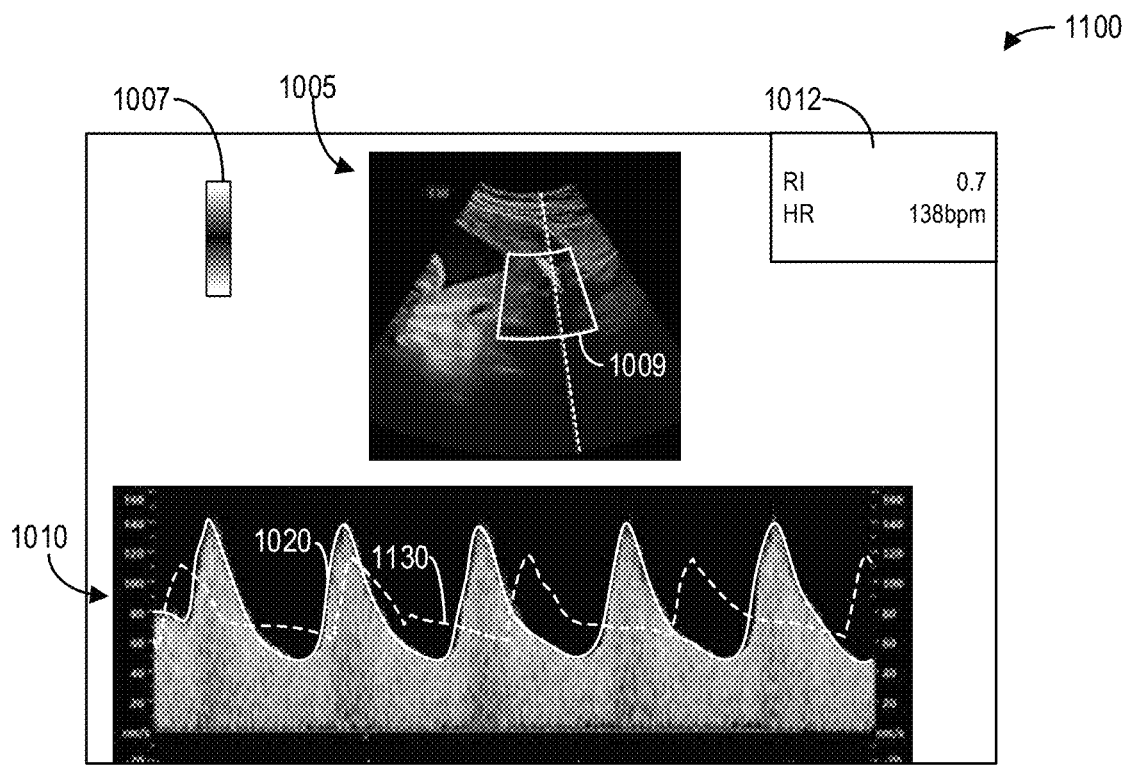
FIG. 11 shows an example display output of a graphical user interface showing the pathological Doppler flow profile of FIG. 10 with a normal flow profile overlaid thereon according to an embodiment.
Figure 12:
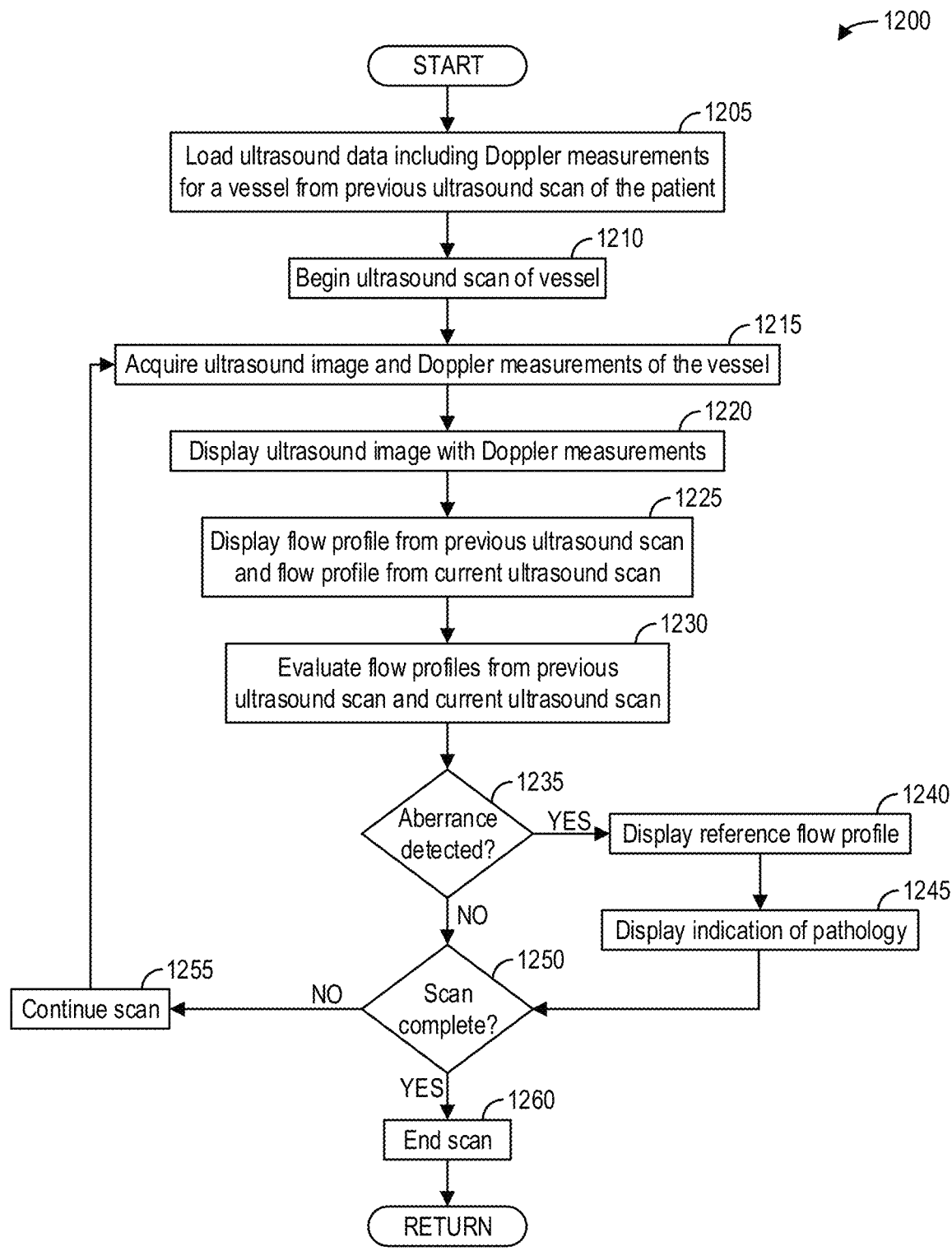
FIG. 12 shows a high-level flow chart illustrating an example method for ultrasound imaging with automatic analysis of Doppler flow patterns during a follow-up examination according to an embodiment.

The following description relates to various embodiments of ultrasound imaging. In particular, systems and methods for detecting flow abnormalities in Doppler ultrasound imaging. The flow abnormalities may be detected in a Doppler spectrum generated from Doppler ultrasound data acquired with an ultrasound imaging system, such as the ultrasound imaging system shown in FIG. 1. In obstetrical sonography, fetal organ screening is among the most applied applications. A major part of the exams is the Doppler-sonographic analysis of fetal and maternal blood vessels, such as the maternal uterine artery, the fetal umbilical artery, the fetal aorta, the fetal mid-cerebral artery, and the fetal ductal vein. If the fetal well-being is disturbed, for example due to an under-supply of oxygen and nutrients from the placenta, a fetal distress cascade may occur wherein first the flow is initially disturbed at the maternal uterine artery, then later the flow is disturbed at the fetal umbilical artery, and so on over time. By the time the flow is disturbed at the fetal mid-cerebral artery, the state of the fetus is critical. Typically the fetal heart rate is monitored and abnormalities in the fetal heart rate are used to provide a diagnosis of fetal distress. However, potential misinterpretation of the fetal heart rate may result in over-diagnosis of fetal distress and unnecessary intervention through emergency cesarean section. Each of the vessels has a very specific flow profile or Doppler spectrum, and so particular measurements of the velocity and certain indices may be used to classify and detect hemodynamic abnormalities. For example, an example image processing system that may be used to detect the abnormalities, such as the image processing system shown in FIG. 2, includes one or more machine learning model trained to automatically detect aberrances of the flow profiles for the vessels of interest. A method for ultrasound imaging, such as the method shown in FIG. 3, may therefore include evaluating the Doppler spectrum or flow profile with a machine learning model during Doppler imaging of a vessel, and displaying an indication of a pathological flow upon detection of an aberrance by the machine learning model. The pathological flow may be indicated to the user of an ultrasound imaging system, for example, by displaying a nominal or normal flow profile over the pathological flow profile. For example, FIG. 4 shows a normal flow profile for a uterine artery displayed in a graphical user interface for ultrasound imaging, while FIG. 5 shows a pathologic flow profile for a uterine artery. When such a pathologic flow profile is detected, the abnormality may be highlighted or indicated via the graphical user interface to the user. For example, as shown in FIG. 6, a normal flow profile for the same vessel may be displayed in the graphical user interface, for example by superimposing the normal profile over the pathologic flow profile. In other examples, the normal flow profile may be adjusted, for example by time-aligning the normal flow profile such that the cycle peaks are aligned with the peaks of the pathologic flow profile, as depicted in FIG. 7. In addition, in some examples, the graphical user interface may specifically highlight or indicate the portions of the pathologic flow profile that deviate from the normal flow profile, as depicted in FIG. 8. In some examples, the normal flow profile may be time-aligned and scaled, as depicted in FIG. 9, to further match the abnormal flow profile such that the differences between the flow profiles is emphasized. An example of another pathologic flow for a uterine artery and an example indication of such pathologic flow is depicted in FIGS. 10 and 11. Further, Doppler measurements from a previous ultrasound scan of a patient may be retrieved during a follow-up ultrasound examination, as depicted in FIG. 12.

Figure 1:
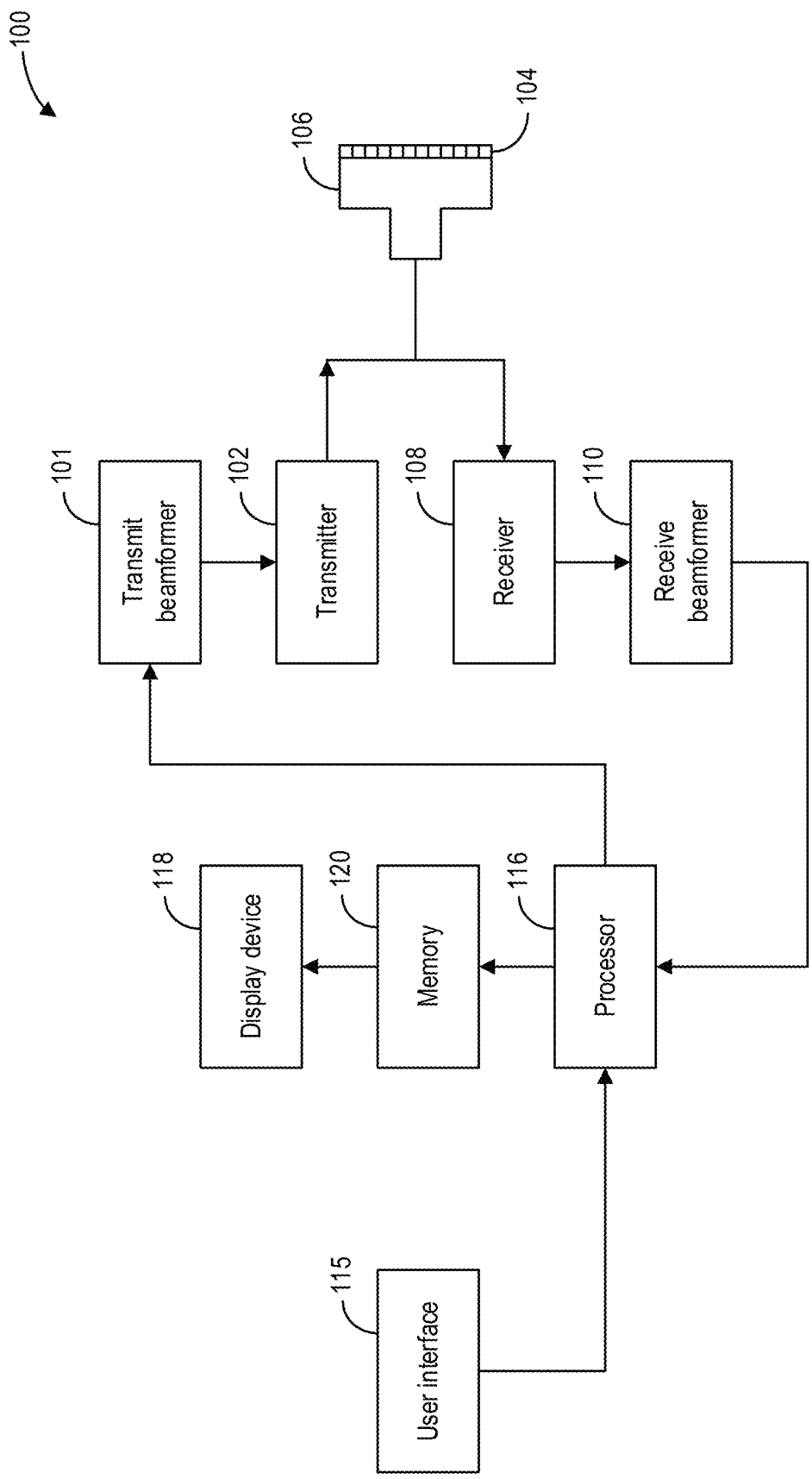
FIG. 1 shows a block schematic diagram illustrating an example ultrasound imaging system according to an embodiment.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, slow flow HD, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In one example, the ultrasound imaging system 100 may be configured to operate in a spectral Doppler mode wherein the ultrasound imaging system 100 obtains a pulse wave Doppler spectrum or continuous wave Doppler spectrum (referred to herein as a Doppler spectrum or flow profile) that includes blood flow velocity data for multiple heart cycles (e.g., beats). Examples of a Doppler spectrum displayed via the display device 118 of the ultrasound imaging system 100 are shown in FIGS. 4-11, as described further herein below.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. In other examples of the present disclosure, the display device 118 and/or the user interface 115 may be integrated into a remote computing system positioned locally, such as a review workstation, or remotely (e.g., for telemedicine). Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Figure 2:
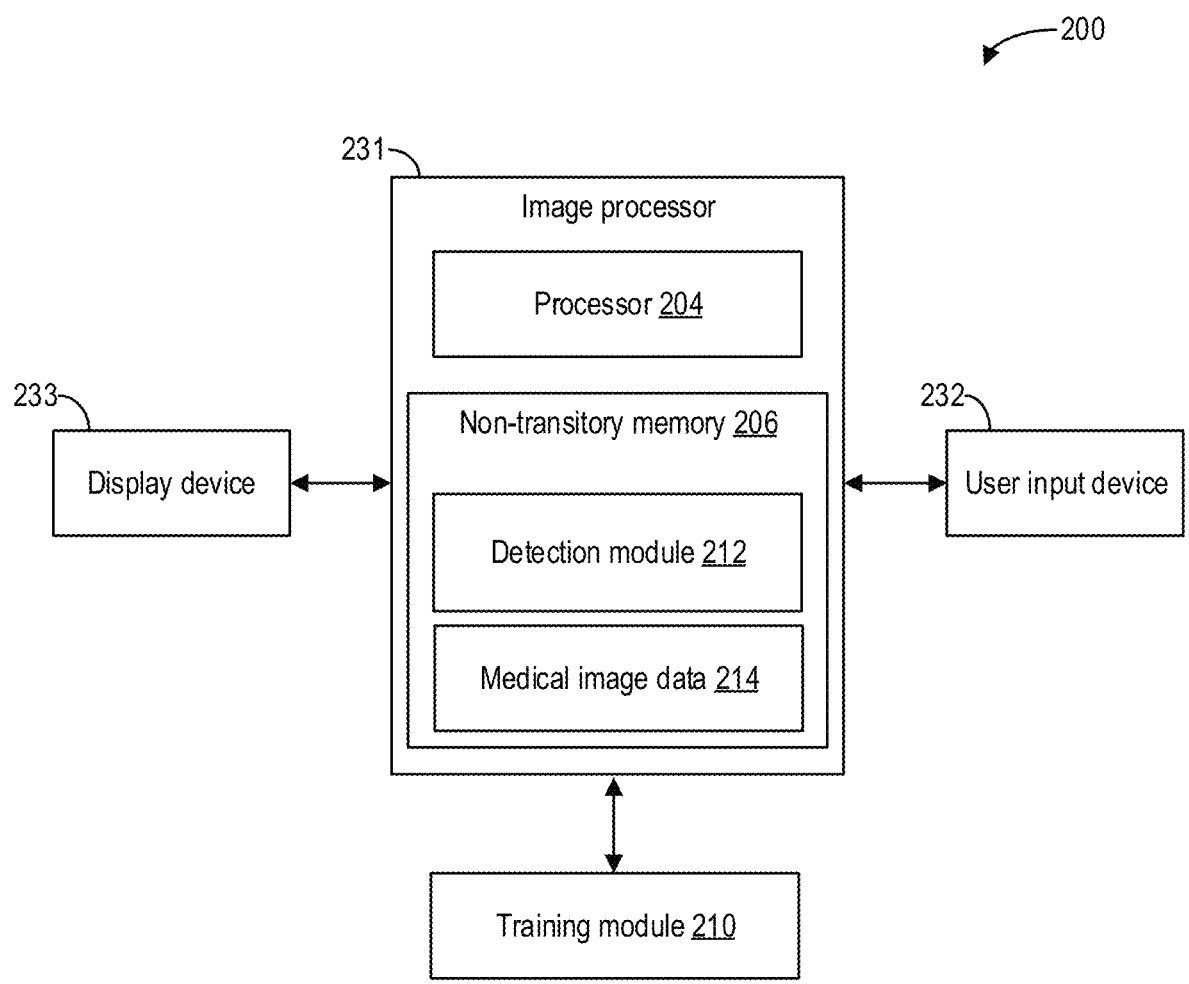
FIG. 2 is a schematic diagram illustrating an image processing system for detecting and classifying abnormalities in Doppler ultrasound measurements according to embodiment.

Referring to FIG. 2, an example medical image processing system 200 is shown. In some embodiments, the medical image processing system 200 is incorporated into a medical imaging system, such as an ultrasound imaging system (e.g., the ultrasound imaging system 100 of FIG. 1), an MRI system, a CT system, a single-photon emission computed tomography (SPECT) system, etc. In some embodiments, at least a portion of the medical image processing system 200 is disposed at a device (e.g., an edge device or server) communicably coupled to the medical imaging system via wired and/or wireless connections. In some embodiments, the medical image processing system 200 is disposed at a separate device (e.g., a workstation) that can receive images from the medical imaging system or from a storage device that stores the images generated by the medical imaging system. The medical image processing system 200 may comprise an image processor 231, a user input device 232, and a display device 233. For example, the image processor 231 may be operatively/communicatively coupled to the user input device 232 and the display device 233.

The image processor 231 includes a processor 204 configured to execute machine readable instructions stored in non-transitory memory 206. The processor 204 may be single core or multi-core, and the programs executed by the processor 204 may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration. In some embodiments, the processor 204 may include other electronic components capable of carrying out processing functions, such as a digital signal processor, a field-programmable gate array (FPGA), or a graphics board. In some embodiments, the processor 204 may include multiple electronic components capable of carrying out processing functions. For example, the processor 204 may include two or more electronic components selected from a plurality of possible electronic components, including a central processor, a digital signal processor, a field-programmable gate array, and a graphics board. In still further embodiments, the processor 204 may be configured as a graphical processing unit (GPU), including parallel computing architecture and parallel processing capabilities.

In the embodiment shown in FIG. 2, the non-transitory memory 206 stores a detection module 212 and medical image data 214. The medical image data 214 may comprise ultrasound imaging data including but not limited to B-mode ultrasound image data, color Doppler ultrasound image data, and Doppler spectra or flow profiles acquired via an ultrasound imaging system such as ultrasound imaging system 100. The detection module 212 includes one or more artificial intelligence algorithms, including machine learning models, to process input medical images from the medical image data 214. Specifically, the detection module 212 may provide an artificial intelligence system for identifying patient abnormalities within the medical image data 214, and specifically for identifying abnormal flow or pathological flow in the Doppler spectra or flow profiles of the medical image data 214. For example, the detection module 212 may include one or more deep learning networks comprising a plurality of weights and biases, activation functions, loss functions, gradient descent algorithms, and instructions for implementing the one or more deep learning networks to process input medical images. Additionally or alternatively, the detection module 212 may store instructions for implementing a neural network, such as a convolutional neural network, for detecting and classifying potential flow abnormalities in the Doppler spectra or flow profiles of the medical image data 214. In such examples, the flow profile may be input to the neural network as an image. Alternatively, the waveform depicted in a flow profile may be input to the neural network as a time series. In such examples, the machine learning model or neural network may be constructed and configured for receiving a time series as input rather than an image.

The detection module 212 may include trained neural networks and may further include training routines, or parameters (e.g., weights and biases), associated with one or more neural network models stored therein. The detection module 212 may further include image recognition algorithms, shape or edge detection algorithms, anatomical structure segmentation and classification algorithms, and the like. In some embodiments, the detection module 212 may evaluate the medical image data 214 as it is acquired in real-time. Additionally or alternatively, the detection module 212 may evaluate the medical image data 214 offline, not in real-time. The detection module 212 may further include a trained machine learning model for automatic vessel segmentation and classification as well as a trained machine learning model or algorithm for automatic Doppler cursor placement inside the vessel for data acquisition.

In some embodiments, the patient abnormalities may include abnormal flow or pathologies in an anatomical feature imaged in the medical image data 214. For example, when the anatomical feature is a vessel, the patient abnormalities include abnormal flow relative to nominal flow for the vessel. In some examples, the detection module 212 includes a plurality of machine learning models for a plurality of vessels, wherein each machine learning model is trained on flow profiles for a particular vessel. For example, the detection module 212 may include a machine learning model trained on flow profiles for a uterine artery, a machine learning model trained on flow profiles for a mid-cerebral artery, a machine learning model trained on flow profiles for an umbilical artery, and so on. In other examples, the detection module 212 may include a machine learning model trained on flow profiles for a plurality of vessels.

The image processor 231 may be communicatively coupled to a training module 210, which includes instructions for training one or more of the machine learning models stored in the detection module 212. The training module 210 may include instructions that, when executed by a processor, cause the processor to build a model (e.g., a mathematical model) based on sample data to make predictions or decisions regarding the detection and classification of patient abnormalities without the explicit programming of a conventional algorithm that does not utilize machine learning. In one example, the training module 210 includes instructions for receiving training data sets from the medical image data 214. The training data sets comprise sets of Doppler flow profiles, associated ground truth labels, and associated model outputs for use in training one or more of the machine learning models stored in the detection module 212. The training module 210 may receive Doppler flow profiles, associated ground truth labels, and associated model outputs for use in training the one or more machine learning models from sources other than the medical image data 214, such as other image processing systems, the cloud, and so on. In some embodiments, one or more aspects of the training module 210 may include remotely-accessible networked storage devices configured in a cloud computing configuration. Further, in some embodiments, the training model 210 is included in the non-transitory memory 206. Additionally or alternatively, in some embodiments, the training model 210 may be used to generate the detection module 212 offline and remote from the image processing system 200. In such embodiments, the training module 210 may not be included in the image processing system 200 but may generate data stored in the image processing system 200.

The non-transitory memory 206 further stores the medical image data 214. The medical image data 214 includes, for example, functional and/or anatomical images captured by an imaging modality, such as ultrasound imaging systems, MRI systems, CT systems, PET systems, etc. As one example, the medical image data 214 may include ultrasound images, such as ultrasound B-mode images, color Doppler image data, and Doppler flow profiles.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices in a cloud computing configuration. As one example, the non-transitory memory 206 may be part of a picture archiving and communication system (PACS) that is configured to store patient medical histories, imaging data, test results, diagnosis information, management information, and/or scheduling information, for example.

The image processing system 200 may further include the user input device 232. The user input device 232 may comprise one or more of a touchscreen, a keyboard, a mouse, a trackpad, a motion sensing camera, or other device configured to enable a user to interact with and manipulate data stored within the image processor 231. As an example, the user input device 232 may enable a user to analyze and rank imaged structures and/or respond to notification prompts.

The display device 233 may include one or more display devices utilizing any type of display technology. In some embodiments, the display device 233 may comprise a computer monitor and may display unprocessed images, processed images, parametric maps, and/or exam reports. The display device 233 may be combined with the processor 204, the non-transitory memory 206, and/or the user input device 232 in a shared enclosure or may be a peripheral display device. The display device 233 may include a monitor, a touchscreen, a projector, or another type of display device, which may enable a user to view medical images and/or interact with various data stored in the non-transitory memory 206. In some embodiments, the display device 233 may be included in a smartphone, a tablet, a smartwatch, or the like.

It may be understood that the medical image processing system 200 shown in FIG. 2 is one non-limiting embodiment of an image processing system, and other imaging processing systems may include more, fewer, or different components without parting from the scope of this disclosure. Further, in some embodiments, at least portions of the medical image processing system 200 may be included in the ultrasound imaging system 100 of FIG. 1, or vice versa (e.g., at least portions of the ultrasound imaging system 100 may be included in the medical image processing system 200). Further, while the medical image processing system 200 may comprise a separate image processing system from a medical imaging system such as the ultrasound imaging system 100, in some examples the medical image processing system 200 may be integrated into the ultrasound imaging system 100. For example, the processor 204 and the non-transitory memory 206 may comprise the processor 116 and the memory 120, respectively, while the user input device 232 and the display device 233 comprise the user interface 115 and the display device 118, respectively.

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory. Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 3:
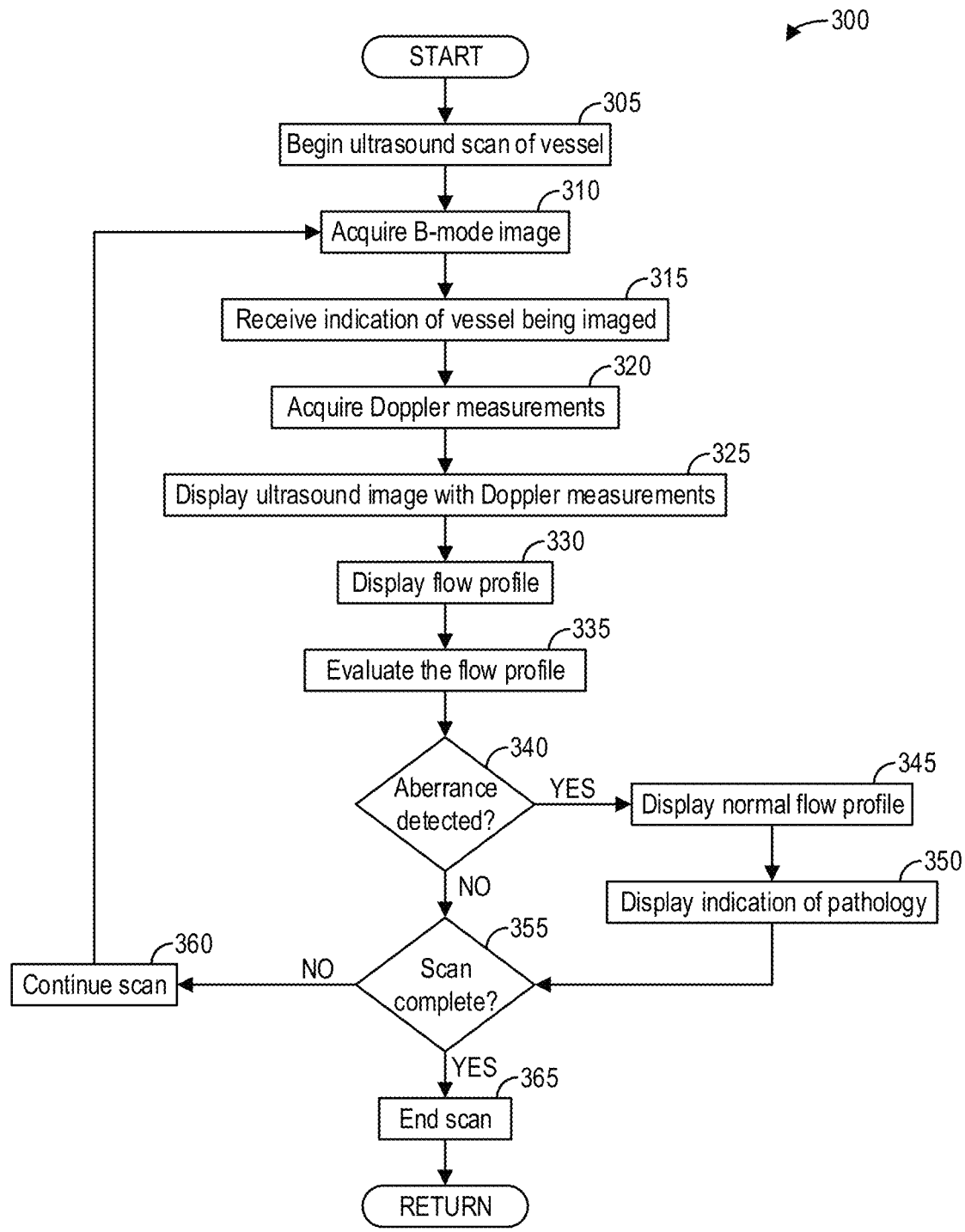
FIG. 3 shows a high-level flow chart illustrating an example method for ultrasound imaging with automatic analysis of Doppler flow patterns according to an embodiment.

FIG. 3 shows a high-level flow chart illustrating an example method 300 for ultrasound imaging with automatic analysis of Doppler flow patterns according to an embodiment. In particular, method 300 relates to evaluating ultrasound Doppler measurements to detect abnormal blood flow in vessels. Method 300 is described with regard to the systems and components of FIGS. 1 and 2, though it should be appreciated that the method 300 may be implemented with other systems and components without departing from the scope of the present disclosure. Method 300 may be implemented as executable instructions in the non-transitory memory 120 and/or the non-transitory memory 206, for example, and may be executed by the processor 116 and/or the processor 204 to perform the actions described hereinbelow.

Method 300 begins at 305. At 305, method 300 begins an ultrasound scan of a vessel. For example, method 300 controls the transmit beamformer 101 and the transmitter 102 to drive the transducer elements 104 of the probe 106 to emit ultrasonic waves into the patient towards the vessel, and further controls the receiver 108 and the receive beamformer 110 to detect, via the transducer elements 104 of the probe 106, the echoes of the ultrasonic waves as described hereinabove. Method 300 may thus control the components of the ultrasound imaging system 100 according to a Doppler ultrasound imaging protocol. In this way, at 310, method 300 acquires a B-mode image or grayscale ultrasound image of the vessel.

At 315, method 300 receives an indication of the vessel being imaged. For example, method 300 may receive an indication of the vessel being imaged via the user interface 115 and/or the user input device 232. That is, the user of the ultrasound imaging system 100 may manually select or otherwise input the vessel being imaged from a menu, for example, and thus method 300 receives the indication of the vessel being imaged. In such examples, method 300 may receive the indication of the vessel being imaged prior to beginning the ultrasound scan at 305. As another example, method 300 may perform image classification of the B-mode image or ultrasound image acquired at 310 to automatically detect the vessel, and so method 300 may receive the indication of the vessel being imaged via the image classification. In such examples, method 300 may perform the image classification with a trained convolutional neural network, as an illustrative example, or another suitable image classification technique, such as segmenting the vessel in the ultrasound image and comparing the segmented vessel to a dictionary of vessel segments to identify the vessel. As described further herein, method 300 also acquires Doppler measurements, and so in some examples method 300 may perform automatic image classification of color or power Doppler images or on the spectral Doppler image itself. Further, the vessel being imaged may be identified using both segmentation and classification trained machine learning model(s). For example, the vessel may be segmented from the image data with a segmentation machine learning model, and the segmented vessel may be classified with a classification machine learning model, or alternatively a single machine learning model may both segment and classify the vessel.

At 320, method 300 acquires Doppler measurements. For example, method 300 may control the components of the ultrasound imaging system 100 as described hereinabove to operate in a spectral Doppler mode and acquire blood flow velocity data and a Doppler spectrum or flow profile for at least several heart beats or cycles. The Doppler cursor (i.e., the positioning of the Doppler ROI or the area being imaged according to the Doppler imaging mode) may be automatically positioned according to the indication of the vessel being imaged. For example, method 300 may automatically identify the position of the vessel being imaged at 315, and automatically position the Doppler cursor at the position of the vessel for Doppler data acquisition. Furthermore, method 300 may compute various measurements or indices based on the acquired Doppler data. For example, the Doppler measurements may also include calculations of the resistive index (RI) and/or the pulsatility index (PI) from the blood flow velocity data and/or the Doppler spectrum, wherein the resistive index comprises the difference between the peak systolic velocity and the end diastolic velocity divided by the peak systolic velocity, and the pulsatility index comprises the difference between the peak systolic velocity and the end diastolic velocity divided by the time averaged velocity.

After acquiring the Doppler measurements, method 300 continues to 325. At 325, method 300 displays an ultrasound image with the Doppler measurements. For example, method 300 may display the blood flow velocity data as color flow image data superimposed on the ultrasound B-mode image. Further, at 330, method 300 displays the flow profile acquired at 320. The flow profile or Doppler spectrum may be displayed adjacent to the ultrasound B-mode image with the color flow image data superimposed thereon in the graphical user interface displayed, for example, via the display device 118 or the display device 233. Method 300 may also display the additional Doppler measurements, such as the calculated RI and/or PI, in the graphical user interface.

At 335, method 300 evaluates the flow profile. In one example, method 300 may evaluate the flow profile with a machine learning model. For example, method 300 may input one or more of the flow profile, the additional Doppler measurements (e.g., the RI and/or the PI), and the B-mode image into one or more machine learning models of the detection module 212, for example. The machine learning model(s) are trained on a plurality of normal or nominal flow profiles for each vessel. In some examples, the indication of the vessel being imaged may be used to evaluate the flow profile. For example, in some examples, the indication of the vessel being imaged may be input along with the flow profile, for example, to a machine learning model trained on normal flow profiles for a plurality of vessels. In such examples, the machine learning model may also output an indication of the vessel being imaged based on the flow profile. In this way, if the vessel actually being imaged is different than the vessel indicated in the indication of the vessel being imaged received at 315, method 300 may identify an error based on a comparison of the indication of the vessel output by the machine learning model and the indication of the vessel received at 315. In such examples, method 300 may optionally display a notification requesting confirmation of the vessel being imaged, as one example. In other examples, method 300 may select a machine learning model trained on normal flow profiles for the vessel being imaged from a plurality of machine learning models, wherein each machine learning model is trained on normal flow profiles for different vessels.

The machine learning model(s) may be configured to output an indication of whether the flow profile is normal, or similarly, an indication that the flow profile exhibits an aberrance or an abnormality relative to normal flow profiles. In some examples, the machine learning model(s) may be further configured to output an identification or indication of the portions of the flow profile that are aberrant or abnormal relative to the normal flow profiles.

In some examples, the machine learning model(s) may be trained on pathologic flow profiles as well as normal flow profiles. The training data for training the machine learning model may thus include normal flow profiles labeled as normal and pathologic flow profiles labeled as pathologic. Further, for different types of pathologic flow profiles, the training data may further include an indication of the type of pathology exhibited by the pathologic flow profile. That is, various pathologies may be associated with a given vessel and may cause different types of flow, and the machine learning model may be trained on training data including a plurality of abnormal flow profiles associated with different pathologies, as well as labels of the pathology responsible for the abnormal flow. The machine learning model may, in such examples, be configured to output an indication of the type of pathology exhibited by the pathologic flow profile when the machine learning model outputs an indication that the flow profile is pathologic or abnormal. Additionally, the flow profile may be characterized or graded according to a flow grading system. For example, a flow profile may be graded as absent (e.g., no flow), minimal, blunted, dampened, stenotic, or normal. Abnormal flow profiles with different grades may be labeled with the grades for training the machine learning model(s) such that the machine learning model(s) may output a grade for the flow profile input to the machine learning model(s).

In other examples, method 300 may evaluate the flow profile with signal processing methods other than a machine learning model for signal analysis. For example, method 300 may perform a time series analysis, a Fourier analysis, a wavelet-based analysis, combinations thereof, and the like, to identify abnormalities and/or to grade the flow profile.

After evaluating the flow profile, method 300 continues to 340. At 340, method 300 determines whether an aberrance is detected in the flow profile. If an aberrance is not detected ("NO"), method 300 continues to 355. However, if an aberrance is detected ("YES"), method 300 continues to 345. At 345, method 300 displays a normal flow profile for the vessel. For example, method 300 may retrieve a normal flow profile for the vessel from a library of normal flow profiles, such as the flow profiles stored in the training module 210 for example. Further, the normal flow profile may be selected from a plurality of normal flow profiles for the vessel stored in the library of normal flow profiles, for example, based on acquisition parameters so that the normal flow profile corresponds to a flow that may be expected given the acquisition. The normal flow profile may be displayed adjacent to the flow profile, in some examples. In other examples, the normal flow profile is superimposed on the flow profile in the graphical user interface. In this way, the user may easily identify the differences between the flow profile from the normal flow profile. In some examples, the normal flow profile may be adjusted based on the flow profiled prior to superimposing the normal flow profile. For example, the normal flow profile may be time aligned such that at least one peak (e.g., an R wave) of the normal flow profile is aligned with a peak of the flow profile. An example of adjusting the normal flow profile to be time-aligned with the flow profile is described further herein with regard to FIG. 7. Additionally, the normal flow profile may be scaled, for example, so that the amplitude of the at least one peak time-aligned with the peak of the flow profile is also equal to the amplitude of the peak of the flow profile. An example of adjusting the normal flow profile in this way is described further herein with regard to FIG. 9.

At 350, method 300 displays an indication of a pathology. For example, method 300 may highlight aberrant portions of the flow profile, for example by adjusting the display of the flow profile at the aberrant portions. As another example, method 300 may graphically highlight the difference between the flow profile and the normal flow profile. For example, method 300 may automatically highlight the portion of the flow profile that is different from the normal flow profile. As another example, method 300 may colorize the portion of the flow profile that is normal a first color (e.g., green) and colorize portions that are different with a second color (e.g., red). As yet another example, method 300 may display an indication of the type of pathology responsible for the abnormalities of the flow profile. In examples wherein the machine learning model is configured to classify the flow profile according to a flow grading system, method 300 may also display the classification or flow grade (e.g., absent, minimal, blunted, dampened, stenotic, normal, and so on) of the flow profile in the graphical user interface.

At 355, method 300 determines whether the scan is complete. The scan may be complete when the user of the ultrasound imaging system 100, for example, indicates via user interface 115 that the scan is complete. If the scan is not complete ("NO"), method 300 continues to 360 to continue the scan. To continue the scan, method 300 returns to 310, for example, to acquire an additional B-mode image and continue acquiring Doppler measurements. In some examples, method 300 may alternatively return to 320 to acquire additional Doppler measurements without acquiring an additional B-mode image. Method 300 thus continues acquiring Doppler measurements and evaluating the flow profile or Doppler spectrum to determine whether a pathological flow is present until the scan is complete. Once the scan is complete ("YES") at 355, method 300 proceeds to 365. At 365, method 300 ends the scan. Method 300 then returns.

Thus, systems and methods for automatically detecting abnormal flow profiles and indicating the abnormalities of the flow profiles are provided. While the method 300 described hereinabove relates to evaluating the Doppler measurements in real-time during an ultrasound scan, it should be appreciated that the method 300 may be adapted for use as a post-processing technique, for example, after ultrasound data including Doppler measurements are acquired. For example, rather than acquiring and evaluating the ultrasound data in real-time during an ultrasound scan, the ultrasound data including the Doppler measurements may be acquired first during an ultrasound scan, then saved in non-transitory memory (for example as medical image data 214 in the non-transitory memory 206 of the medical image processing system 200). The ultrasound data including the Doppler measurements may then be evaluated with the machine learning model(s) as described hereinabove to determine whether the flow is pathological or abnormal, and the Doppler spectrum or flow profile may be displayed with a normal flow profile superimposed thereon. Additionally, an indication of the abnormalities in the flow profile may be highlighted in the display of the flow profile. Further, when the user executes a Scan Assistant protocol or script to perform a patient examination, the user may configure when the image undergoes automatic detection of abnormality in flow hemodynamics, as well as what additional actions (if any) in case of abnormality the system may automatically perform (e.g., extra measurements, and so on). The detected abnormality findings may then be automatically populated for the user as comments/annotations and will be automatically populated into the reporting software.

As illustrative and non-limiting examples of how abnormal flow profiles may be indicated to a user, FIGS. 4-11 depict example graphical user interfaces for displaying ultrasound data including Doppler spectra. The graphical user interfaces described herein may be displayed, for example, via the display device 118 of the ultrasound imaging system 100, or via the display device 233 of the medical image processing system 200. As an illustrative and non-limiting example, FIG. 4 shows an example display output of a graphical user interface 400 showing a Doppler spectrum or flow profile 410 for a vessel with a normal flow. The graphical user interface 400 displays an ultrasound image 405 comprising a grayscale or B-mode image with color flow image data (e.g., velocity measurements) superimposed thereon in a color flow region of interest (ROI) 409. The graphical user interface 400 may further include a color scale 407 positioned adjacent to the ultrasound image 405 to illustrate the velocities of the colors depicted in the color flow image data of the ultrasound image 405. The graphical user interface 400 further displays the Doppler spectrum or flow profile 410 for the vessel positioned in the color flow ROI 409. The graphical user interface 400 further displays a flow profile trace 420 of the flow profile 410 which may be automatically generated based on the flow profile 410.

The graphical user interface 400 further includes a measurement parameter display 412 that displays one or more Doppler measurements and other measurements. For example, as depicted, the measurement parameter display 412 includes a measurement of the resistive index (RI) as well as the heart rate (HR). It should be appreciated that other measurements may be displayed in the measurement parameter display 412, such as average maximum blood flow velocity, average mean blood flow velocity, average maximum pressure gradient of the blood flow velocity, average velocity time integral, average envelope time, pulsatility index, and so on. In some examples, these measurements may be calculated based on the flow profile trace 420.

It should be appreciated that the graphical user interface 400 may include additional components, such as a menu (not shown) including options for controlling or adjusting the acquisition parameters of the ultrasound imaging system and/or the display parameters for the graphical user interface 400.

In the depicted example, the vessel being imaged comprises a uterine artery. For a normal uterine artery, the resistive index is typically 0.5 or lower. For a pathologic flow in the uterine artery, the resistive index may be 0.6 or higher. As the flow profile is normal, FIG. 5 shows an example display output of a graphical user interface 500 showing a Doppler flow profile 510 for a vessel with a pathological flow. In particular, the vessel comprises a uterine artery. Similar to the graphical user interface 400, the graphical user interface 500 includes an ultrasound image 505 comprising a grayscale or B-mode image with color flow image data superimposed thereon within the color flow ROI 509, a color scale 507, and a measurement parameter display 512. A flow profile trace 520 corresponding to the upper boundary of the flow profile 510 is displayed on the flow profile 510.

The first indication of a negative trend in the flow of the uterine artery is a notch after the systolic sloping, which is clearly visible in the flow profile 510, along with a resistive index above 0.6, as depicted. This notch may comprise an aberrance or abnormality relative to the normal flow profile 420 of a uterine artery.

When such a pathologic flow profile is detected, the abnormality may be highlighted or indicated via the graphical user interface to the user. For example, as shown in the graphical user interface 600 of FIG. 6, a normal flow profile 630 for the same vessel may be displayed in the graphical user interface 600, for example by superimposing the normal flow profile 630 over the pathologic flow profile 510. The normal flow profile 630 may comprise the flow profile trace 420 of the normal flow profile 410, as depicted, though it should be appreciated that in some examples, the normal flow profile 410 may be superimposed or otherwise displayed along with the pathologic flow profile 510. By displaying the normal flow profile 630 over the flow profile 510, a user viewing the graphical user interface 600 may thus be notified that the flow profile 510 is abnormal or pathological.

Further, though not depicted in the graphical user interface 600, in some examples the resistive index may be highlighted as the value for the given vessel indicates that the flow profile is pathologic. For example, the display of the measurement parameter display 512 may be adjusted to highlight (e.g., by adjusting the color of the text or by adding a background color to the text) the resistive index (RI) within the measurement parameter display 512.

In other examples, the normal flow profile 630 may be adjusted, for example by time-aligning the normal flow profile 630 such that the cycle peaks are aligned with the peaks of the pathologic flow profile 510. For example, FIG. 7 shows an example graphical user interface 700 wherein a normal flow profile 730 is displayed over the pathologic flow profile 510, wherein the normal flow profile 730 corresponds to the normal flow profile 630 with the first peak time-aligned with the first peak of the flow profile 510.

As another example, the display of the portions of the pathologic flow profile 510 that are aberrant or abnormal may be adjusted to highlight the abnormalities. For example, FIG. 8 shows an example graphical user interface 800 wherein the flow profile trace 520 of the flow profile 510 is replaced with a flow profile trace 820. Specifically, the flow profile trace 820 comprises the flow profile trace 520, wherein display of the portions 841, 842, 843, 844, 845, 846, and 847 of the flow profile trace 820 are adjusted to highlight the aberrance of the portions from the normal flow profile 730. As depicted, the portions 841, 842, 843, 844, 845, 846, and 847 are dashed rather than solid, though it should be appreciated that the portions 841, 842, 843, 844, 845, 846, and 847 may be colorized (e.g., displayed in red) while the remainder of the flow profile trace 820 is displayed in another color (e.g., green) to emphasize or highlight the portions 841, 842, 843, 844, 845, 846, and 847.

In some examples, the normal flow profile may be time-aligned and scaled to further match the abnormal flow profile such that the differences between the flow profiles is emphasized. For example, FIG. 9 shows an example graphical user interface 900 wherein a normal flow profile 930 is displayed or superimposed over the flow profile 510. Specifically, the normal flow profile 930 corresponds to the normal flow profile 630 wherein the first peak is time-aligned with the first peak of the flow profile 510 as well as scaled such that the amplitudes are matched, as depicted. In this way, the differences between the flow profiles 930 and 510 are easily discernable by the user viewing the graphical user interface 900 via a display device such as display device 115 or display device 233. Further, the flow profile trace 920 of the flow profile 510 may be adjusted similar to the flow profile trace 820 to further emphasize the difference between the normal flow profile 930 and the flow profile 510. Alternatively, as depicted, visual indicators 941, 942, 943, 944, 945, 946, and 947 may be superimposed on the flow profile trace 930 to indicate the locations of the aberrances detected by the machine learning model.

An example of another pathologic flow for a uterine artery and an example indication of such pathologic flow is depicted in FIGS. 10 and 11. In particular, FIG. 10 shows an example graphical user interface 1000 displaying a Doppler spectrum or flow profile 1010 for a uterine artery with a pathological flow. In contrast with the pathologic flow of the flow profile 510, the flow profile 1010 exhibits pathologic flow via a substantially low diastolic flow with a resistive index above 0.6. The graphical user interface 1000 further includes an ultrasound image 1005 with a color flow image data superimposed within the color flow ROI 1009, a color scale 1007, and a measurement parameter display 1012.

As described hereinabove, the flow profile 1010 may be evaluated by a machine learning model trained on a plurality of normal and/or abnormal flow profiles for a uterine artery, which in turn determines that the flow profile 1010 is abnormal or pathologic relative to normal flow profiles. To indicate the abnormality of the flow profile 1010 to the user, a normal flow profile may be superimposed thereon. For example, FIG. 11 shows an example display output of a graphical user interface 1100 showing the pathological Doppler flow profile 1010 of FIG. 10 with a normal flow profile 1130 overlaid thereon. The normal flow profile 1130 may comprise, as depicted, the flow profile trace 420 for the normal flow profile 410, without adjustments to the timing and scale of the flow profile trace 420. In other examples, as described hereinabove with regard to FIGS. 7-9, the normal flow profile 1130 may be time-aligned with the flow profile 1010, and additionally or alternatively may be scaled such that the amplitude of the peaks match. Further, the flow profile trace 1020 may be adjusted to indicate the portions of the flow profile trace 1020 that are abnormal relative to the normal flow profile 1130. Additionally or alternatively, visual indicators may be displayed or superimposed onto the flow profile 1010 to indicate the portions of the flow profile 1010 that are abnormal.

For other vessels, such as the mid-cerebral artery, the umbilical artery, the ductal vein, and so on, the particular shape of the normal and pathologic flow profiles may be different from the normal and pathologic flow profiles of the uterine artery. As such, the resistive indices for normal and pathologic flows may also be different from the uterine artery. For example, for a mid-cerebral artery, a normal flow profile may exhibit a low, flat diastolic flow with a resistive index in the range of 0.8 to 0.85, while a pathologic flow profile may exhibit a clearly increased diastolic flow with a resistive index below 0.7. As another example, for an umbilical artery, the normal flow profile may exhibit a diastolic flow with a resistive index ranging from 0.6 to 0.8, while a pathologic flow profile may exhibit a too-low or missing diastolic flow with a resistive index above 0.8. As yet another example, for a ductal vein, a normal flow profile may exhibit an m-shaped flow with no complete incision in the end diastole, where as a pathologic flow profile exhibits an incision reaching down to the zero-line or even a reverse flow.

FIG. 12 shows a high-level flow chart illustrating an example method 1200 for ultrasound imaging with automatic analysis of Doppler flow patterns during a follow-up examination according to an embodiment. In particular, method 1200 relates to evaluating ultrasound Doppler measurements to detect abnormal blood flow in vessels. Method 1200 is described with regard to the systems and components of FIGS. 1 and 2, though it should be appreciated that the method 300 may be implemented with other systems and components without departing from the scope of the present disclosure. Method 1200 may be implemented as executable instructions in the non-transitory memory 120 and/or the non-transitory memory 206, for example, and may be executed by the processor 116 and/or the processor 204 to perform the actions described hereinbelow.

Method 1200 begins at 1205. At 1205, method 1200 loads ultrasound data including Doppler measurements for a vessel acquired during a previous ultrasound scan of a patient. Continuing at 1210, method 1200 begins an ultrasound scan of the vessel. For example, method 1200 controls the transmit beamformer 101 and the transmitter 102 to drive the transducer elements 104 of the probe 106 to emit ultrasonic waves into the patient towards the vessel, and further controls the receiver 108 and the receive beamformer 110 to detect, via the transducer elements 104 of the probe 106, the echoes of the ultrasonic waves as described hereinabove. Method 1200 may thus control the components of the ultrasound imaging system 100 according to a Doppler ultrasound imaging protocol. In this way, at 1215, method 300 acquires a B-mode image or grayscale ultrasound image of the vessel as well as Doppler measurements of the vessel. Method 1200 may additionally automatically detect the position and type of the vessel, as described hereinabove, and automatically position the Doppler cursor at the position of the vessel to acquire the Doppler measurements.

Continuing at 1220, method 1200 displays the ultrasound image with the Doppler measurements acquired at 1215, for example, via the display device 118 or the display device 233. Further, at 1225, method 1200 displays the flow profile from the previous ultrasound scan retrieved at 1205 as well as the flow profile from the current ultrasound scan acquired at 1215. The flow profiles may be displayed side-by-side in the graphical user interface displayed via the display device 118 or the display device 233. As the previous flow profile and the current flow profile are acquired at a time T1 and a time T1+ΔT, respectively, the user may review both flow profiles to monitor disease progression or treatment effect.

At 1230, method 1200 evaluates the flow profiles from the previous ultrasound scan and the current ultrasound scan. For example, method 1200 may input both flow profiles to a trained machine learning model as discussed hereinabove to identify potential abnormalities in either flow profile. If the flow profile from the previous ultrasound scan was previously evaluated for potential abnormalities, the previous results of the analysis of the previous flow profile may be retrieved from storage rather than analyzing the flow profile during the current scan.

After evaluating the flow profiles, method 1200 continues to 1235. At 1235, method 1200 determines whether an aberrance is detected in either of the flow profiles. If an aberrance is not detected ("NO"), method 1200 continues to 1250. However, if an aberrance is detected ("YES"), method 1200 continues to 1240. At 1240, method 1200 displays a normal or reference flow profile for the vessel. For example, method 1200 may retrieve a reference flow profile for the vessel from a library of normal or reference flow profiles, such as the flow profiles stored in the training module 210 for example. Further, the reference flow profile may be selected from a plurality of reference flow profiles for the vessel stored in the library of reference flow profiles, for example, based on acquisition parameters so that the reference flow profile corresponds to a flow that may be expected given the acquisition. The reference flow profile may be displayed adjacent to the flow profile containing the abnormality or aberrance, in some examples. In other examples, the reference flow profile is superimposed on the flow profile(s) featuring the aberrance in the graphical user interface. In this way, the user may easily identify the differences between the flow profiles from the reference flow profile. In some examples, the reference flow profile may be adjusted based on the flow profile prior to superimposing the reference flow profile. For example, the reference flow profile may be time aligned such that at least one peak (e.g., an R wave) of the reference flow profile is aligned with a peak of the flow profile. Additionally, the reference flow profile may be scaled, for example, so that the amplitude of the at least one peak time-aligned with the peak of the flow profile is also equal to the amplitude of the peak of the flow profile.

At 1245, method 1200 displays an indication of a pathology. For example, method 1200 may highlight aberrant portions of the flow profiles, for example by adjusting the display of the flow profiles at the aberrant portions. As another example, method 1200 may graphically highlight the difference between the flow profile and the reference flow profile, as well as the difference between the current flow profile and the previous flow profile. For example, method 1200 may automatically highlight the portion of the flow profile that is different from the reference flow profile and/or the previous flow profile. As another example, method 1200 may colorize the portion of the flow profile that is normal a first color (e.g., green) and colorize portions that are different with a second color (e.g., red). As yet another example, method 1200 may display an indication of the type of pathology responsible for the abnormalities of the flow profile(s). In examples wherein the machine learning model is configured to classify the flow profile(s) according to a flow grading system, method 1200 may also display the classification or flow grade (e.g., absent, minimal, blunted, dampened, stenotic, normal, and so on) of the flow profile(s) in the graphical user interface.

At 1250, method 1200 determines whether the scan is complete. The scan may be complete when the user of the ultrasound imaging system 100, for example, indicates via user interface 115 that the scan is complete. If the scan is not complete ("NO"), method 1200 continues to 1255 to continue the scan. To continue the scan, method 1200 returns to 1215, for example, to acquire an additional B-mode image and continue acquiring Doppler measurements. Method 1200 thus continues acquiring Doppler measurements and evaluating the flow profile or Doppler spectrum to determine whether a pathological flow is present until the scan is complete. Once the scan is complete ("YES") at 1250, method 1200 proceeds to 1260. At 1260, method 1200 ends the scan. Method 1200 then returns.

Thus, during a follow-up examination, a flow profile or Doppler spectrum from a previous exam as well as a flow profile for the current exam may be displayed side-by-side to the user. Further, both flow profiles may be evaluated to detect abnormalities in the flow hemodynamics, and both results may be presented to the user for disease/treatment monitoring. Furthermore, the evaluation of flow profiles described herein may be performed after the ultrasound examination(s). For example, the Doppler spectra from one or more previous ultrasound examinations may be retrieved and evaluated for abnormalities, with results displayed to the user as described hereinabove.

A technical effect of the disclosure includes the display of a normal flow profile over a pathologic flow profile. Another technical effect of the disclosure includes the display of a flow profile in a graphical user interface with pathologic or abnormal portions of the flow profile highlighted in the graphical user interface. Yet another technical effect of the disclosure includes the automatic detection of abnormalities in a Doppler spectrum. Another technical effect of the disclosure includes an indication of a type of pathology automatically identified in a Doppler spectrum.

In one embodiment, a method comprises acquiring, via an ultrasound probe, Doppler measurements over a plurality of cardiac cycles, evaluating a flow profile comprising the Doppler measurements to detect an abnormality in the flow profile, and displaying, via a display device, the flow profile with a reference flow profile overlaid thereon.

In a first example of the method, the method further comprises adjusting display of the flow profile to highlight one or more portions of the flow profile exhibiting the abnormality. In a second example of the method optionally including the first example, adjusting the display of the flow profile to highlight the one or more portions of the flow profile exhibiting the abnormality comprises colorizing the one or more portions of the flow profile exhibiting the abnormality a first color and colorizing a remainder of the flow profile a second color. In a third example of the method optionally including one or more of the first and second examples, the method further comprises superimposing visual indicators on the flow profile to highlight the one or more portions of the flow profile exhibiting the abnormality. In a fourth example of the method optionally including one or more of the first through third examples, the method further comprises acquiring the Doppler measurements for a vessel, wherein the reference flow profile is based on one or more flow profiles for the vessel without pathologies. In a fifth example of the method optionally including one or more of the first through fourth examples, the method further comprising acquiring an ultrasound image of the vessel, and detecting the vessel being imaged based on the ultrasound image, wherein detecting the vessel being imaged comprises detecting one or more of a location of the vessel being imaged and a type of the vessel being imaged, and wherein detecting the vessel being imaged comprises one of automatically detecting, with a machine learning model trained for vessel classification, the vessel being imaged based on the ultrasound image, or receiving a manual selection, via user input, of the vessel being imaged in the ultrasound image. In a sixth example of the method optionally including one or more of the first through fifth examples, evaluating the flow profile comprises evaluating the flow profile with a trained machine learning model, the trained machine learning model selected from a plurality of trained machine learning models based on the type of the vessel being imaged. In a seventh example of the method optionally including one or more of the first through sixth examples, the method further comprises automatically positioning a Doppler cursor at the position of the vessel being imaged for acquiring the Doppler measurements. In an eighth example of the method optionally including one or more of the first through seventh examples, the method further comprises adjusting display of the reference flow profile to at least partially match the flow profile, wherein adjusting the display of the reference flow profile includes one or more of time-aligning a peak of the reference flow profile with a peak of the flow profile, and scaling the reference flow profile to match an amplitude of the peak of reference flow profile with an amplitude of the peak of the flow profile. In a ninth example of the method optionally including one or more of the first through eighth examples, the method further comprises determining, with the trained machine learning model, a type of pathology associated with the abnormality of the flow profile, and displaying, via the display device, an indication of the type of pathology.

In another embodiment, a method comprises acquiring, via an ultrasound probe, an ultrasound image of a vessel, acquiring, via the ultrasound probe, Doppler measurements of blood flow within the vessel, displaying, via a display device, a graphical user interface including the ultrasound image with color flow data of the Doppler measurements superimposed thereon, and a flow profile constructed from the Doppler measurements, detecting, with a trained machine learning model, an abnormality in the flow profile, displaying, via the display device, a reference flow profile for the vessel superimposed on the flow profile in the graphical user interface, and adjusting display of the flow profile in the graphical user interface to indicate the abnormality.

In a first example of the method, detecting the abnormality in the flow profile comprises inputting the flow profile to the trained machine learning model, and receiving an indication of the abnormality as output from the trained machine learning model. In a second example of the method optionally including the first example, the flow profile is input to the trained machine learning model as an image. In a third example of the method optionally including the first example, the flow profile is input to the trained machine learning model as a time series. In a fourth example of the method optionally including one or more of the first through third examples, the method further comprises adjusting a scale and timing of the reference flow profile to at least partially match the flow profile prior to superimposing the reference flow profile on the flow profile in the graphical user interface.

In yet another embodiment, an ultrasound imaging system comprises an ultrasound probe, a display device, and a processor configured with executable instructions in non-transitory memory that when executed cause the processor to: acquire, via the ultrasound probe, Doppler measurements over a plurality of cardiac cycles; evaluate a flow profile comprising the Doppler measurements to detect an abnormality in the flow profile; and display, via the display device, the flow profile with a reference flow profile overlaid thereon.

In a first example of the system, the processor is further configured with executable instructions in the non-transitory memory that when executed cause the processor to adjust display of the flow profile to highlight one or more portions of the flow profile exhibiting the abnormality. In a second example of the system optionally including the first example, the processor is further configured with executable instructions in the non-transitory memory that when executed cause the processor to adjusting the display of the flow profile to highlight the one or more portions of the flow profile exhibiting the abnormality by colorizing the one or more portions of the flow profile exhibiting the abnormality a first color and colorizing a remainder of the flow profile a second color. In a third example of the system optionally including one or more of the first and second examples, the processor is further configured with executable instructions in the non-transitory memory that when executed cause the processor to acquire the Doppler measurements for a vessel, and select the reference flow profile from a plurality of reference flow profiles according to the vessel being imaged. In a fourth example of the system optionally including one or more of the first through third examples, the processor is further configured with executable instructions in the non-transitory memory that when executed cause the processor to train a machine learning model with training data including one or more of a plurality of reference flow profiles and a plurality of abnormal flow profiles, and evaluate the flow profile with the trained machine learning model to detect the abnormality. In a fifth example of the system optionally including one or more of the first through fourth examples, the processor is further configured with executable instructions in the non-transitory memory that when executed cause the processor to determine, with the trained machine learning model, a type of pathology associated with the abnormality of the flow profile, and display, via the display device, an indication of the type of pathology.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring, via an ultrasound probe, an ultrasound image of a vessel;
   acquiring, via the ultrasound probe, Doppler measurements of blood flow within the vessel;
   displaying, via a display device, a graphical user interface including the ultrasound image with data of the Doppler measurements, and a flow profile constructed from the Doppler measurements of blood flow within the vessel;
   detecting, with a detection module, an abnormality in the flow profile, wherein the flow profile is input to the detection module as an image or as a time series of the flow profile; and
   adjusting the display of the graphical user interface to indicate the abnormality via displaying, via the display device, a reference flow profile for the vessel superimposed over the flow profile in the graphical user interface, wherein adjusting the display includes one or more of time-aligning a peak of the reference flow profile with a peak of the flow profile, and scaling the reference flow profile to match an amplitude of the peak of reference flow profile with an amplitude of the peak of the flow profile.

2. The method of claim 1, wherein detecting the abnormality in the flow profile comprises inputting the flow profile to the detection module, and receiving an indication of the abnormality as output from the detection module based on the flow profile matching an abnormality in a reference flow profile of the vessel.

3. The method of claim 1, wherein detecting the abnormality in the flow profile comprises inputting the flow profile to the detection module, and receiving an indication of the abnormality as output from the detection module based on a difference between the flow profile and the reference flow profile of the vessel.

4. The method of claim 1, further comprising adjusting a scale and timing of the reference flow profile to match the flow profile prior to superimposing the reference flow profile on the flow profile in the graphical user interface.

5. The method of claim 1, wherein adjusting the display includes both time-aligning a peak of the reference flow profile with a peak of the flow profile and scaling the reference flow profile to match an amplitude of the peak of reference flow profile with an amplitude of the peak of the flow profile.

6. The method of claim 1, wherein adjusting the display includes both time-aligning a plurality of peaks of the reference flow profile with a plurality of peaks of the flow profile, and scaling the reference flow profile to match an amplitude of the peak of reference flow profile with an amplitude of the peak of the flow profile.

* * * * *